(12) United States Patent
Kameyama

(10) Patent No.: US 8,748,158 B2
(45) Date of Patent: Jun. 10, 2014

(54) MICROORGANISM HAVING GASTRIC-JUICE PROMOTING ACTIVITY, AND ITS SECRETORY PRODUCT

(76) Inventor: Yoshichika Kameyama, Habikino (JP)

( * ) Notice: Subject to any disclaimer, the term of this patent is extended or adjusted under 35 U.S.C. 154(b) by 638 days.

(21) Appl. No.: 12/090,482

(22) PCT Filed: Aug. 10, 2007

(86) PCT No.: PCT/JP2007/065772
§ 371 (c)(1),
(2), (4) Date: Apr. 17, 2008

(87) PCT Pub. No.: WO2009/022399
PCT Pub. Date: Feb. 19, 2009

(65) Prior Publication Data
US 2010/0291052 A1    Nov. 18, 2010

(51) Int. Cl.
*C12N 1/20*    (2006.01)
(52) U.S. Cl.
USPC ..................... 435/252.5; 424/93.46
(58) Field of Classification Search
None
See application file for complete search history.

(56) References Cited

U.S. PATENT DOCUMENTS 4,393,225 A  *  7/1983  Hayashi et al. ............... 549/289

OTHER PUBLICATIONS

Database GenBank [online], Accessin No. AB195283, /www.ncbi.nlm.nih.gov/ entrez/viewer.fcgi?66347569:OLD:419493> May 20, 2005 uploaded, Pham, V. T. et al., Definition: *Bacillus pumilus* gene for 16s rRNA, strain: Tb1.*

* cited by examiner

*Primary Examiner* — Irene Marx
(74) *Attorney, Agent, or Firm* — James W. Judge

(57) ABSTRACT

Designed to afford a novel microorganism promoting gastric juice secretion and having platelet increasing activity, and to afford a pharmaceutical agent composed of a product secreted by the novel microorganism. The novel microorganism, international deposit number: NITE BP-295, belongs to the species *Bacillus pumilus*, and is characterized by taking either form of coccus and *bacillus*, and makes figure-eight movement. The novel microorganism of the present invention is the novel microorganism having the gene represented by SEQ ID No: 1, and an object of the present invention is to afford the microorganism and a gastric juice secretion-promoting composition composed of the product secreted by the novel microorganism.

3 Claims, 10 Drawing Sheets

FIG. 1

[BLAST Top 20]

Sequences producing significant alignments:

| | Score (bits) | E Value |
|---|---|---|
| gi\|45269058\|gb\|AY548955.1\| Bacillus pumilus strain S9 16S r... | 2926 | 0.0 |
| gi\|45269052\|gb\|AY548949.1\| Bacillus pumilus strain 8N-4 16S... | 2926 | 0.0 |
| gi\|45934529\|gb\|AY505512.1\| Bacillus pumilus strain GSP61 16... | 2902 | 0.0 |
| gi\|16973340\|emb\|AJ315067.1\|BSP315067 Bacillus sp. 19499 16S... | 2892 | 0.0 |
| gi\|34809007\|gb\|AY373359.1\| Bacillus pumilus strain c10 16S ... | 2878 | 0.0 |
| gi\|46560693\|gb\|AY587832.1\| Bacterium Te68R 16S ribosomal RN... | 2872 | 0.0 |
| gi\|14009321\|gb\|AY030327.1\| Bacillus pumilus strain KL-052 1... | 2870 | 0.0 |
| gi\|45934531\|gb\|AY505514.1\| Bacillus sp. GSP46 16S ribosomal... | 2859 | 0.0 |
| gi\|10129890\|dbj\|AB048252.1\| Bacillus pumilus gene for 16S r... | 2859 | 0.0 |
| gi\|27530897\|dbj\|AB098578.1\| Bacillus pumilus gene for 16S r... | 2839 | 0.0 |
| gi\|40888887\|gb\|AY289549.1\| Bacillus pumilus strain SA175001... | 2833 | 0.0 |
| gi\|30171831\|gb\|AY260861.1\| Bacillus pumilus strain WN694 16... | 2821 | 0.0 |
| gi\|21748162\|emb\|AJ494730.1\|BPU494730 Bacillus pumilus parti... | 2821 | 0.0 |
| gi\|27497691\|gb\|AY167884.1\| Bacillus pumilus 16S ribosomal R... | 2817 | 0.0 |
| gi\|27497690\|gb\|AY167883.1\| Bacillus pumilus 16S ribosomal R... | 2817 | 0.0 |
| gi\|27497688\|gb\|AY167881.1\| Bacillus pumilus 16S ribosomal R... | 2817 | 0.0 |
| gi\|27497687\|gb\|AY167880.1\| Bacillus pumilus 16S ribosomal R... | 2817 | 0.0 |
| gi\|33354180\|dbj\|AB115957.1\| Bacillus pumilus gene for 16S r... | 2817 | 0.0 |
| gi\|46560675\|gb\|AY587814.1\| Bacterium Te29R 16S ribosomal RN... | 2811 | 0.0 |
| gi\|3970889\|dbj\|AB020208.1\| Bacillus pumilus DNA for 16S rib... | 2809 | 0.0 |

FIG. 2

[Top hit]
>gi|45269058|gb|AY548955.1| Bacillus pumilus strain S9 16S ribosomal RNA gene, complete sequence
Length = 1544

Score = 2926 bits (1476), Expect = 0.0
Identities = 1479/1480 (99%)
Strand = Plus / Plus

```
Query: 1   tcgagcggacagaaggggagcttgctcccggatgttagcggcggacgggtgagtaacacgt 60
           ||||||||||||||||||||||||||||||||||||||||||||||||||||||||||||
Sbjct: 55  tcgagcggacagaaggggagcttgctcccggatgttagcggcggacgggtgagtaacacgt 114
```

FIG. 3

```
Query:  61  gggtaacctgcctgtaagactgggataactccgggaaaccggagctaataccggatagtt 120
            ||||||||||||||||||||||||||||||||||||||||||||||||||||||||||| |
Sbjct: 115  gggtaacctgcctgtaagactgggataactccgggaaaccggagctaataccggatagat 174

Query: 121  ccttgaaccgcatggttcaaggatgaaagacggtttcggctgtcacttacagatggaccc 180
            ||||||||||||||||||||||||||||||||||||||||||||||||||||||||||||
Sbjct: 175  ccttgaaccgcatggttcaaggatgaaagacggtttcggctgtcacttacagatggaccc 234

Query: 181  gcggcgcattagctagttggtggggtaatggctcaccaaggcgacgatgcgtagccgacc 240
            ||||||||||||||||||||||||||||||||||||||||||||||||||||||||||||
Sbjct: 235  gcggcgcattagctagttggtggggtaatggctcaccaaggcgacgatgcgtagccgacc 294

Query: 241  tgagagggtgatcggccacactgggactgagacacggcccagactcctacgggaggcagc 300
            ||||||||||||||||||||||||||||||||||||||||||||||||||||||||||||
Sbjct: 295  tgagagggtgatcggccacactgggactgagacacggcccagactcctacgggaggcagc 354

Query: 301  agtagggaatcttccgcaatggacgaaagtctgacggagcaacgccgcgtgagtgatgaa 360
            ||||||||||||||||||||||||||||||||||||||||||||||||||||||||||||
Sbjct: 355  agtagggaatcttccgcaatggacgaaagtctgacggagcaacgccgcgtgagtgatgaa 414

Query: 361  ggttttcggatcgtaaagctctgttgttagggaagaacaagtgcgagagtaactgctcgc 420
            ||||||||||||||||||||||||||||||||||||||||||||||||||||||||||||
Sbjct: 415  ggttttcggatcgtaaagctctgttgttagggaagaacaagtgcgagagtaactgctcgc 474

Query: 421  accttgacggtacctaaccagaaagccacggctaactacgtgccagcagccgcggtaata 480
            ||||||||||||||||||||||||||||||||||||||||||||||||||||||||||||
Sbjct: 475  accttgacggtacctaaccagaaagccacggctaactacgtgccagcagccgcggtaata 534

Query: 481  cgtaggtggcaagcgttgtccggaattattgggcgtaaagggctcgcaggcggtttctta 540
            ||||||||||||||||||||||||||||||||||||||||||||||||||||||||||||
Sbjct: 535  cgtaggtggcaagcgttgtccggaattattgggcgtaaagggctcgcaggcggtttctta 594

Query: 541  agtctgatgtgaaagcccccggctcaaccggggagggtcattggaaactgggaaacttga 600
            ||||||||||||||||||||||||||||||||||||||||||||||||||||||||||||
Sbjct: 595  agtctgatgtgaaagcccccggctcaaccggggagggtcattggaaactgggaaacttga 654

Query: 601  gtgcagaagaggagagtggaattccacgtgtagcggtgaaatgcgtagagatgtggagga 660
            ||||||||||||||||||||||||||||||||||||||||||||||||||||||||||||
Sbjct: 655  gtgcagaagaggagagtggaattccacgtgtagcggtgaaatgcgtagagatgtggagga 714

Query: 661  acaccagtggcgaaggcgactctctggtctgtaactgacgctgaggagcgaaagcgtggg 720
            ||||||||||||||||||||||||||||||||||||||||||||||||||||||||||||
Sbjct: 715  acaccagtggcgaaggcgactctctggtctgtaactgacgctgaggagcgaaagcgtggg 774

Query: 721  gagcgaacaggattagataccctggtagtccacgccgtaaacgatgagtgctaagtgtta 780
            ||||||||||||||||||||||||||||||||||||||||||||||||||||||||||||
Sbjct: 775  gagcgaacaggattagataccctggtagtccacgccgtaaacgatgagtgctaagtgtta 834

Query: 781  gggggtttccgcccctagtgctgcagctaacgcattaagcactccgcctggggagtacg 840
            ||||||||||||||||||||||||||||||||||||||||||||||||||||||||||||
Sbjct: 835  gggggtttccgcccctagtgctgcagctaacgcattaagcactccgcctggggagtacg 894
```

FIG. 4

```
Query:  841  gtcgcaagactgaaactcaaaggaattgacgggggcccgcacaagcggtggagcatgtgg  900
             ||||||||||||||||||||||||||||||||||||||||||||||||||||||||||||
Sbjct:  895  gtcgcaagactgaaactcaaaggaattgacgggggcccgcacaagcggtggagcatgtgg  954

Query:  901  tttaattcgaagcaacgcgaagaaccttaccaggtcttgacatcctctgacaaccctaga  960
             ||||||||||||||||||||||||||||||||||||||||||||||||||||||||||||
Sbjct:  955  tttaattcgaagcaacgcgaagaaccttaccaggtcttgacatcctctgacaaccctaga  1014

Query:  961  gatagggctttcccttcggggacagagtgacaggtggtgcatggttgtcgtcagctcgtg  1020
             ||||||||||||||||||||||||||||||||||||||||||||||||||||||||||||
Sbjct:  1015 gatagggctttcccttcggggacagagtgacaggtggtgcatggttgtcgtcagctcgtg  1074

Query:  1021 tcgtgagatgttgggttaagtcccgcaacgagcgcaaccccttgatcttagttgccagcat 1080
             ||||||||||||||||||||||||||||||||||||||||||||||||||||||||||||
Sbjct:  1075 tcgtgagatgttgggttaagtcccgcaacgagcgcaaccccttgatcttagttgccagcat 1134

Query:  1081 tcagttgggcactctaaggtgactgccggtgacaaaccggaggaaggtggggatgacgtc 1140
             ||||||||||||||||||||||||||||||||||||||||||||||||||||||||||||
Sbjct:  1135 tcagttgggcactctaaggtgactgccggtgacaaaccggaggaaggtggggatgacgtc 1194

Query:  1141 aaatcatcatgccccttatgacctgggctacacacgtgctacaatggacagaacaaaggg 1200
             ||||||||||||||||||||||||||||||||||||||||||||||||||||||||||||
Sbjct:  1195 aaatcatcatgccccttatgacctgggctacacacgtgctacaatggacagaacaaaggg 1254

Query:  1201 ctgcaagaccgcaaggtttagccaatcccataaatctgttctcagttcggatcgcagtct 1260
             ||||||||||||||||||||||||||||||||||||||||||||||||||||||||||||
Sbjct:  1255 ctgcaagaccgcaaggtttagccaatcccataaatctgttctcagttcggatcgcagtct 1314

Query:  1261 gcaactcgactgcgtgaagctggaatcgctagtaatcgcggatcagcatgccgcggtgaa 1320
             ||||||||||||||||||||||||||||||||||||||||||||||||||||||||||||
Sbjct:  1315 gcaactcgactgcgtgaagctggaatcgctagtaatcgcggatcagcatgccgcggtgaa 1374

Query:  1321 tacgttcccgggccttgtacacaccgcccgtcacaccacgagagtttgcaacacccgaag 1380
             ||||||||||||||||||||||||||||||||||||||||||||||||||||||||||||
Sbjct:  1375 tacgttcccgggccttgtacacaccgcccgtcacaccacgagagtttgcaacacccgaag 1434

Query:  1381 tcggtgaggtaacctttatggagccagccgccgaaggtggggcagatgattggggtgaag 1440
             ||||||||||||||||||||||||||||||||||||||||||||||||||||||||||||
Sbjct:  1435 tcggtgaggtaacctttatggagccagccgccgaaggtggggcagatgattggggtgaag 1494

Query:  1441 tcgtaacaaggtagccgtatcggaaggtgcggctggatca 1480
             ||||||||||||||||||||||||||||||||||||||||
Sbjct:  1495 tcgtaacaaggtagccgtatcggaaggtgcggctggatca 1534
```

MICROORGANISM HAVING GASTRIC-JUICE PROMOTING ACTIVITY, AND ITS SECRETORY PRODUCT

BACKGROUND OF THE INVENTION

1. Technical Field

The present invention, involving a novel microorganism belonging to the species *Bacillus pumilus*, relates to a novel microorganism, and to its secretory products and plasmids employing them, having an activity that prompts the secretion of gastric juice, countering gastric-acid decrease due to chronic gastritis.

2. Description of the Related Art

For gastric ulcers, duodenal ulcers, and other peptic ulcers, drugs (such as gastric-acid secretion blockers, and gastric antacids) that suppress digestive fluids and other visceral-wall invasive factors, and drugs (such as mucoprotective agents) that reinforce defense mechanisms have been used. Nevertheless, although promoting gastric-acid secretion presumably should be effective in patients with chronic gastritis, particularly atrophic gastritis, the present situation is that gastric-juice promoters that are nontoxic to living organisms have not been developed.

In cases of *Helicobacter pylori* infection, which is one of the causes of gastric ulcers, chronic gastritis is engendered, ultimately ending in inducing ulcers and cancer. That is, the bacteria is deleterious to the gastric condition; yet the reality is that a microorganism that improves the gastric condition while being a kindred microbe has yet to be discovered.

Accordingly, the discovery of a gastric-health meliorating microorganism antagonistic to *H. pylori* has been desired. Meanwhile, the manufacture of therapeutic agents utilizing discovered novel microorganisms and their secretory products has been an issue.

BRIEF SUMMARY OF THE INVENTION

According to experiments by the inventors, for an environment that is totally the opposite of *H. pylori*, that is, to counter chronic gastritis—particularly, the type of chronic gastritis in which gastric acid decreases—a novel microorganism of the present invention promotes gastric juice secretion to alleviate the chronic gastritis, and moreover is hypothesized to prevent cancer and ulcers from chronic gastritis. Thus, the novel microorganism can be detected from stomach and blood of all persons, and can also be detected from the blood of patients with chronic gastritis, ulcers, or cancer.

Not only does it have properties advantageous to promoting gastric-juice secretion, but because it also exhibits platelet-, erythrocyte-, and leukocyte-increasing action, it enables multifarious applications.

As a result of animal experiments, effectiveness in promoting gastric juice secretion was confirmed in a novel microorganism (International Deposit Number: NITE BP-295) belonging to the species *Bacillus pumilus*; moreover, it proved to be nontoxic because its $LD_{50}$ is 2 g or more.

This microorganism can be both punctuate and catenulate in form, is 0.5 to 1 µm×10 to 20 µm in size with a flagellum on either end, and has motility, making figure-eight movements. It has spores, and is a highly aerobic gram-positive *bacillus* and coccus. It takes on a catenulate form. The isolation source is the human stomach wall or blood. Alternatively, a virus giving rise to chronic gastritis may be implanted in a fertilized ovum and the antagonizing microbes that appear may be collected.

The cultivation conditions are as below.
Per 1000 ml medium, (trypto-soya broth) are added the nutrients
  peptone—17 g,
  soybean peptone—3 g,
  sodium chloride—5 g,
  glucose—2.5 g, and
  potassium hydrogenphosphate—2.5 g,
and 3 g caustic soda is added in. The pH is adjusted to 8.5. Nutrient medium sterilization conditions: 121° C., perform 15 minutes; cultivation temperature: 37° C.; cultivation period: from 2 to 7 days.

The bacteria cultivated under the above conditions are characterized by being obligatory-aerobic; viability confirmation is by unaided visual observation or by observation under a microscope.

Storage conditions: possible by generally employed methods, including freeze drying.

The novel microorganism thus collected has the following characteristics. It should be noted that they are principally by microscopic observation.
1. When it phagocytoses pathogens, antibacterial properties intensify.
2. Changes form depending on the pathogenic bacterium.
3. Secretory substances that are metabolites are brown.
4. Does not invade erythrocytes. (As to erythrocytes: When ordinary anticancer drugs are employed, the red blood cell count will not decrease—with the Hb remaining 12 to 16, the red blood cell count does not decrease; with hepatitis C, it goes to about 6.)
5. The novel microorganism cleanses dead tissue.
6. The novel microorganism is susceptible to radioactive beams, ultraviolet rays, and microacoustic waves.
7. The novel microorganism is highly heat-resistant—can withstand 100° C. for several hours, and does not lyse. Survives autoclaving.
8. Prompts increase in erythrocytes, platelets, and leukocytes; remedying of anemia is seen.
   (From the fact that in a patient whose leukocyte was 6000, a white-blood-cell count of over 500 was verified even after being administered an anticancer drug, the augmenting action owing to this bacterium was verified. From the fact that in a patient whose platelet was 200,000, it fell only to the 3,000 level even after the patient was administered an anticancer drug, the augmenting action owing to this bacterium was verified.)

Its sequence: Partial sequencing was carried out; proved to have the genetic sequence represented by Seq. No. 1. Furthermore, as illustrated in FIGS. 2 through 4, the microorganism was determined to be, with 99% homology, the species *Bacillus pumilus*. The phylogenetic tree is as in FIG. 5. With the sequence having been partially specified, application to, for example, plasmid expression vectors and other practical uses are possible, and in large-scale culturing, screening, and drug manufacture numerous benefits are anticipated.

The microorganism of the invention was deposited under the Budapest Treaty on the International Recognition of the Deposit of Microorganisms for the Purposes of Patent Procedure as Deposit No. NTE BP-295, with the full taxonomic description "*Bacillus pumilus*," on Dec. 25, 2006, at the Incorporated Administrative Agency, National Institute of Technology and Evaluation, Patent Microorganisms Depositary (NPMD), 2-5-8 Kazusakamatari, Kisarazu-shi, Chiba-ken 292-0818, Japan.

A method of extracting the secretory products is as follows. First, bacteria are cultivated in broth at a temperature of 33 to 37° C. for seven days. Next, pure butyl alcohol, in the same amount as, is added is stirred well into the culture filtrate. After leaving the mixture for three hours, or centrifuging it, the clear butyl alcohol liquid is separated off. Hydrochloric acid is added to the liquid to bring the pH to 3.0, and the mixture is stirred thoroughly and left for 12 hours. The mixture is then vacuum-dried to obtain bright yellow crystals, and organic and inorganic substances.

The solution apart from the butyl alcohol liquid is mixed in with active carbon, stirred well, and left for one day.

Active carbon alone is added to butyl alcohol, and after 12 hours the butyl alcohol eluate is subjected to vacuum drying. Thereafter repeating likewise, crystal is obtained.

The present invention also relates to a method of manufacturing secretory products from the present invention, utilizing a phenotypically transformed microorganism incorporating an expression vector having a DNA sequence such as will code the amino-acid sequence of the secretory product. A phenotypically transformed microorganism according to the present invention is cultivated in the manner described above, and the secretory product is isolated from the nutrient medium.

The novel microorganism of the present invention and its secretory products have activity prompting secretion of gastric acid, and are heat-resistant. The extract is hypothesized to counter chronic gastritis of the type in which gastric acid decreases, and other chronic gastritis, by promoting gastric acid secretion to alleviate the chronic gastritis, and, by regulating the stomach condition, in turn to prevent cancer and ulcers from the chronic gastritis. The bacterium is detected from the stomach and blood of all persons, and occasionally from the blood of patients with chronic gastritis, ulcers, or cancer.

Not only does it have properties advantageous to promoting gastric-juice secretion, but because it also exhibits platelet-, erythrocyte-, and leukocyte-increasing action, and moreover is nontoxic, it enables multifarious applications.

BRIEF DESCRIPTION OF THE SEVERAL VIEWS OF THE DRAWINGS

FIG. 1 is a homology search explanatory diagram.

FIG. 2 is a diagram presenting homology search results (bases 1-60).

FIG. 3 is a diagram presenting homology search results (bases 61-840).

FIG. 4 is a diagram presenting homology search results (bases 841-1480).

DETAILED DESCRIPTION OF THE INVENTION

The present invention becomes apparent from typical embodiments cited in the following examples, but the present invention is not limited to the scope of the examples.

In the embodiments of the present invention, Embodiment 1 first represents cultivation conditions and results, and Embodiment 2 next describes how to separate secretory product off, and animal experiment employing the secretory product. Furthermore, antitumor test (Embodiment 3), toxicity test (Embodiment 4), clinical test (Embodiment 5), staining test (Embodiment 6) are explained.

First Embodiment

This microorganism is punctuate or catenulate in shape and 0.5 to 1 μm×10 to 20 μm in size with flagella on its both ends, and has motility to perform figure-eight movement. Although the microorganism is aerobic gram-positive *bacillus* or coccus with spores, it also takes on catenulate shape. The isolation source is the human stomach wall or blood. The cultivation conditions are as below. Per 1000 ml medium, (tryptosoya broth) are added the nutrients peptone—17 g,
 soybean peptone—3 g,
 sodium chloride—5 g,
 glucose—2.5 g, and
 potassium hydrogenphosphate—2.5 g, and 3 g caustic soda is added in. The pH is adjusted to 8.5. Nutrient medium sterilization conditions: 121° C., perform 15 minutes; cultivation temperature: 37° C.; cultivation period: from 2 to 7 days. (FIGS. 6, 7, 8 and 9.)

Figure 5:
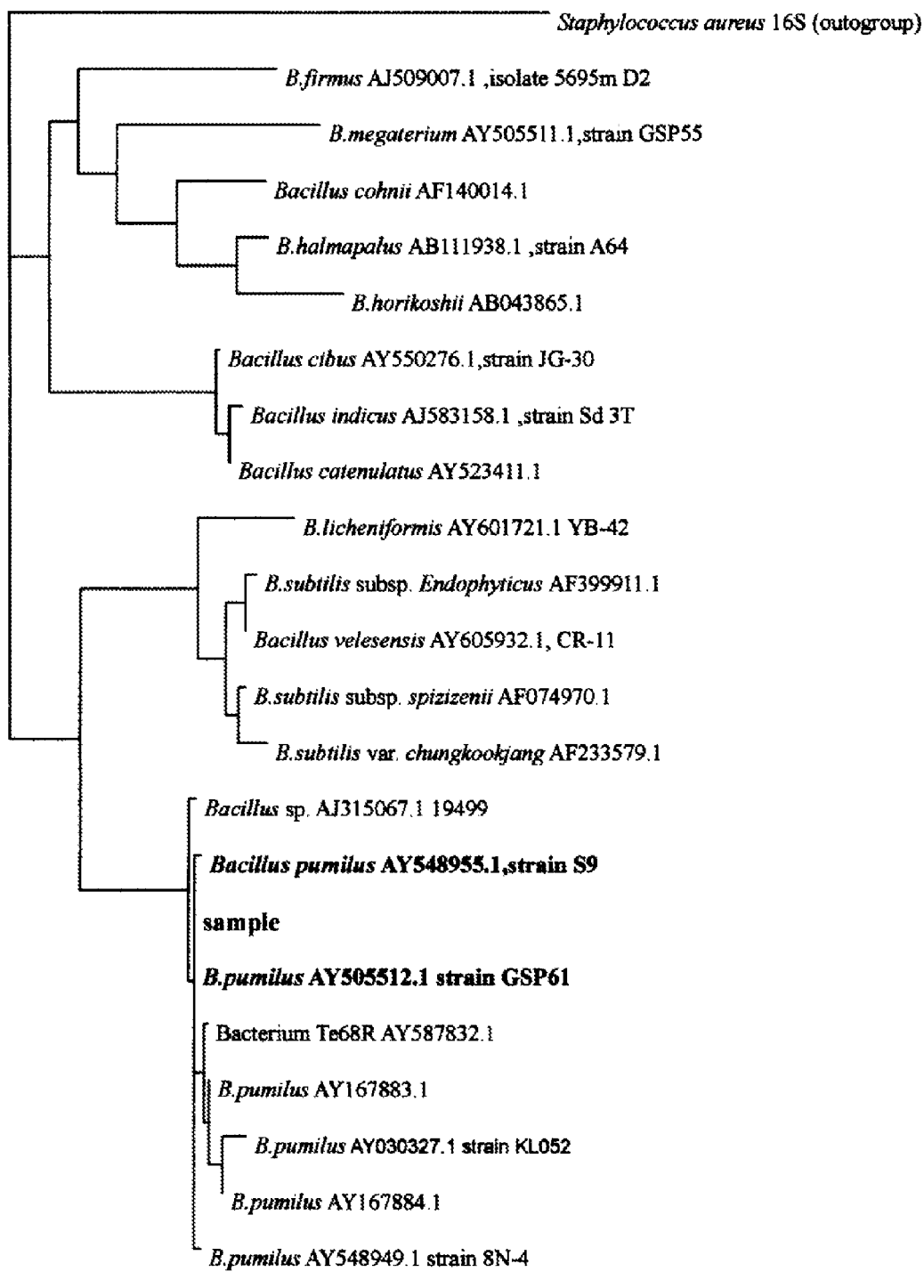
FIG. 5 is a diagram presenting a phylogenetic tree of a novel microorganism of the present invention.
Figure 6:
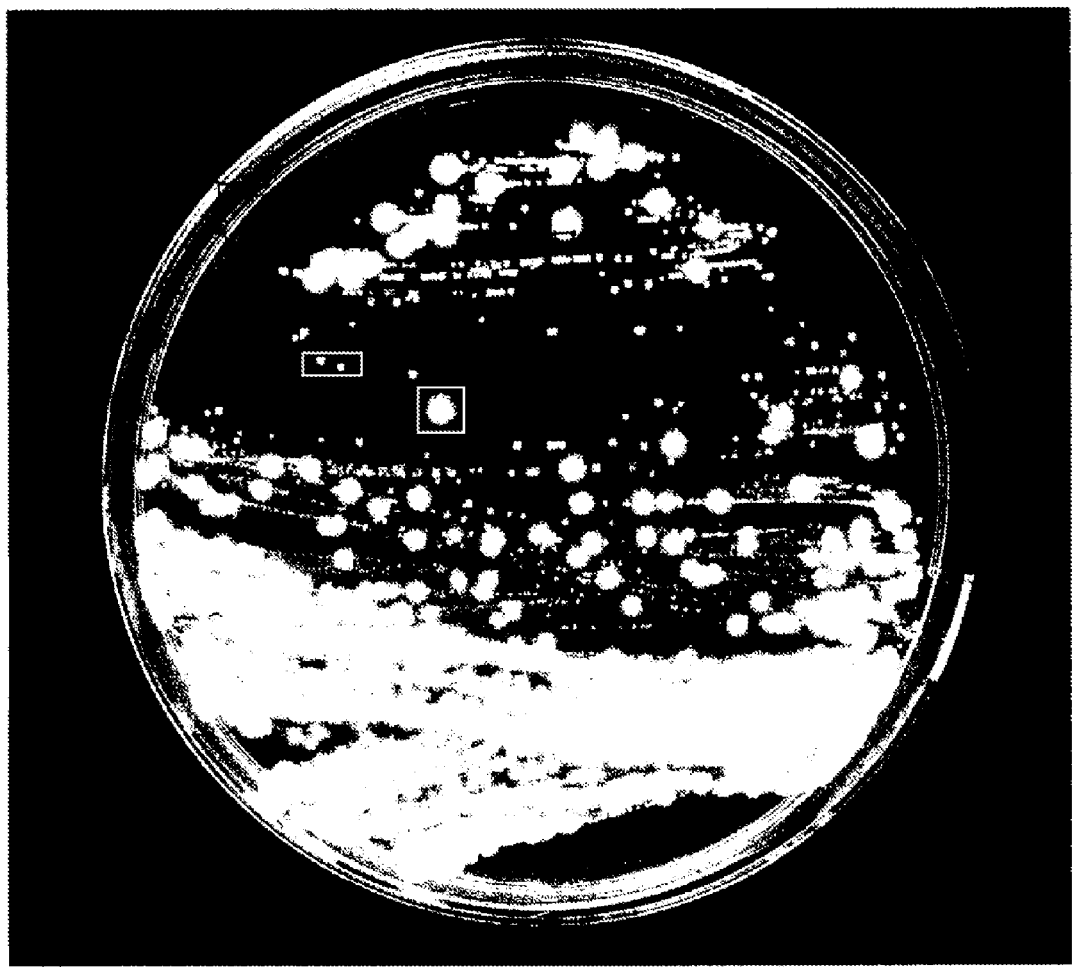
FIG. 6 is a diagram presenting a nutrient-medium colony of the novel microorganism of the present invention.

The bacteria cultivated under the above conditions are characterized by being obligatory-aerobic; viability confirmation is by unaided visual observation or by observation under a microscope. FIG. 6 presents an image of colonies cultivated for one day in the designated medium.

Figure 7:
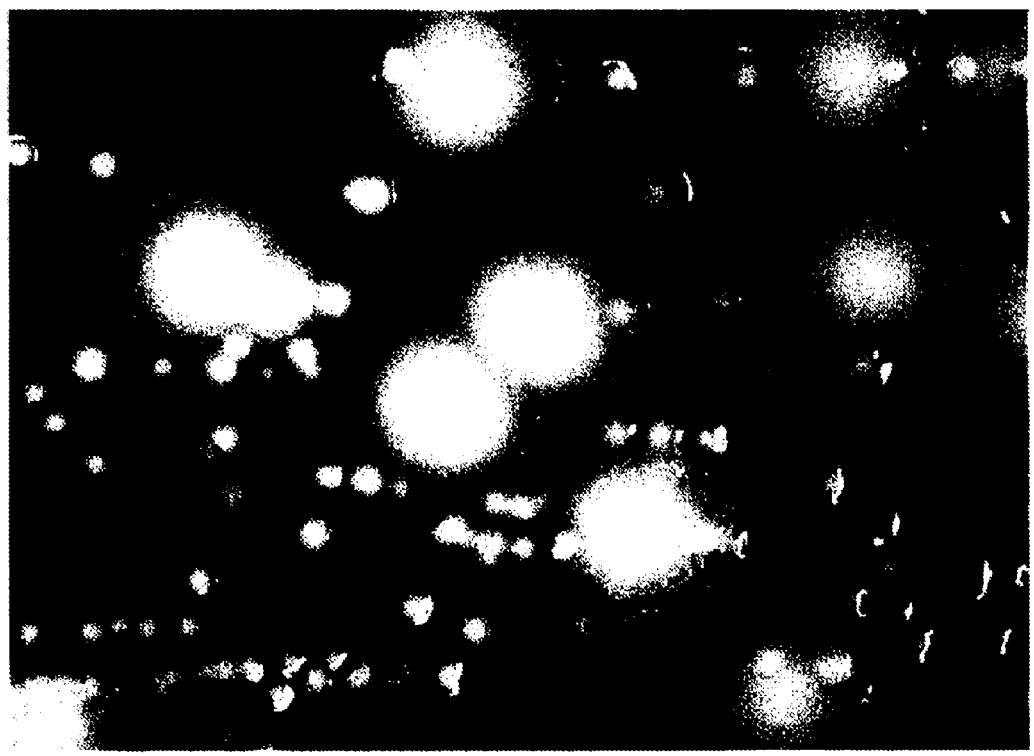
FIG. 7 is an enlarged view of FIG. 6.
Figure 8:
FIG. 8 is a diagram presenting a Gram-stain of a large colony.
Figure 9:
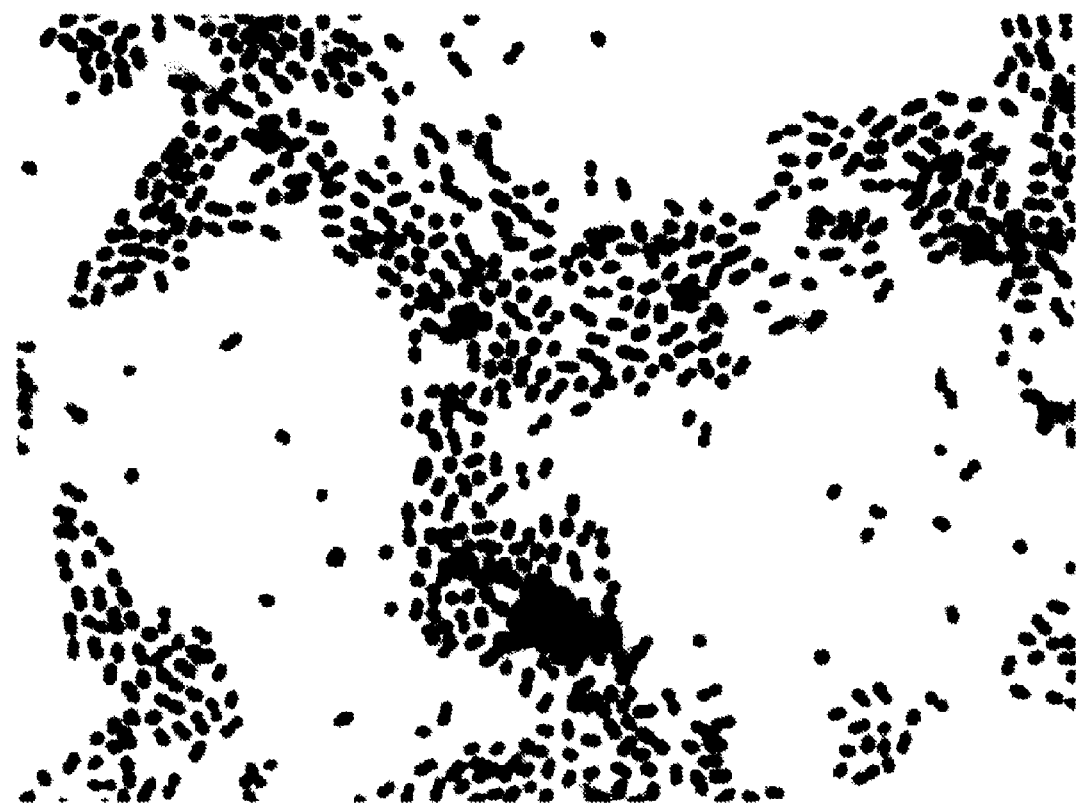
FIG. 9 is a diagram presenting a Gram-stain of a small colony.

Furthermore, that of the colonies which is boxed in a square on the right is the colony whose surface is greatly rough, and that of the colonies which is boxed in a rectangular on the left is the small colony whose surface is smooth. FIG. 7 is an enlarged part of the colonies. Results of Gram-staining demonstrate that the right side colony is gram-positive *bacillus* (FIG. 8), and the left side colony is gram-positive coccus (FIG. 9). As to the conditions under which the bacteria are stored, they can be stored in ways generally employed, including freeze dehydration.

Second Embodiment

As to a change in animal gastric juice, a reaction to secretion-product doses was checked.

How Secretion Product Extracted

The secretory product was extracted in the following manner: The colonies were put in an incubator with temperature of 37° C., and when the surfaces of the colonies became right gray or right yellow surfaces after two to seven days, the colonies were put in broth to cultivate bacteria for seven days at a temperature of 30° C. to 37° C.

Next, into the culture filtrate, the same amount of pure butyl alcohol as the culture filtrate was stirred.

After the culture filtrate into which the butyl alcohol had been stirred was left for three hours, or was centrifuged, clear butyl alcohol solution was separated off.

The butyl alcohol solution was added with decinomal hydrochloric acid to bring pH to 3.0, stirred thoroughly, and left for 12 hours. Subsequently, the solution was vacuum-dried to obtain right yellow crystal, organic and inorganic substances.

A solution other than butyl alcohol solution and active carbon was mixed, stirred thoroughly, and left for one day.

Only active carbon was added to butyl alcohol, and after 12 hours, butyl alcohol eluate was subjected to vacuum-dry. Afterwards, such procedures were repeated to obtain crystal.

Animal Experiment

In Embodiment 2 of the present invention, as to the product secreted by the novel microorganism, a test for measuring the amount of gastric juice secretion in Heidenhain pouch dogs was carried out.

Experimental: As medium, carbohydrate solution was used in the proportion of 5% to the secretory product of 2.6 g (and was stored at room temperatures).

Experimental animal: male dogs purchased at the age of 13 months were for 13 days medically inspected, acclimated, and bread. By observing their normal conditions, and by measuring their weights, whether or not the dogs are healthy animals was checked to use 13 month-old animals whose weights on the day of surgery was from 14.2 to 14.7 kg.

Environment: The experimental environment was arranged in the range in which a temperature was from 20 to 28° C., a relative humidity was from 30 to 80%, the times of ventilation was from 12 to 18 times per hour, lighting hours were 2 hours (from 7:00 to 19:00).

Feed: Labo D Stock® (Nosan Corporation)

Drinking water: Water was taken freely from an automatic feed device in a water supply and sewerage system.

Administration Method: The secretory product of 500 mg was put in a mortar, and then the carbohydrate solution in the proportion of 5% was put in the mortar to dissolve the secretory product with a pestle. The carbohydrate solution was added to the dissolved secretory product so as to be 50 ml, and was rendered a dosing solution.

Dosing solution weight: 10 mg/kg

Dosing solution volume: 1 mL/kg, three examples

Measurement Method: The amount of secreted gastric acid was measured every 15 minutes within 2 hours after the dosing solution was administered, and changes in the secreted gastric acid amount were studied.

Heidenhain Pouch Dog Preparation and Management

The dogs were given nothing to eat for 18 hours or more as of the day before the surgery, and atropine hydrosulfate (0.1 mg/kg) was intramuscularly administered in the dogs 30 minutes before anesthesia induction. Sodium thiopental was given to the dogs from their forelimb cephalic veins to induce anesthesia, and then the dogs were laid on the back on a moisturizing pad of a body temperature controller, with the pad temperature being arranged to be 38° C. on a surgical bed. The dogs' tracheae were then cannulated and they were given artificial respiration and an inhalant anesthetic. The artificial-respiration single inhale/exhale volume was made 20 to 25 mg/kg, at 11 to 13 cylces/min. The inhalant anesthetic was introduced with an added 1 to 4% having been nitrous-oxide gasified, and maintenance anesthesia at 0.5 to 2.0% was carried out. After the hair on and around the dogs' abdominal region was removed with an electric clipper, the entire operating area was sterilized and an incision was made through the skin and muscle layers along a medial line from slightly below the xiphisternum to above the navel region, and then the stomachs were withdrawn from the abdominal cavities to expose the stomachs on the abdominal walls. The blood vessels in the greater curvature of the stomach intersecting with an excision marking line were double-ligated, and cut. After that, the excision marking line was cut and sutured with a gastrointestinal suturing instrument and a gastrostomy tube was set alongside the pouches, and then the opened abdominal region was sutured and the pouch interior was washed several times with a warmed physiological saline solution. The dogs were given nothing to eat within two days from the day after the surgery. During the food deprivation, the dogs received fluid of 150 mL/day (Lactec D®, Otuka Pharmaceutical Co., Ltd). After the food deprivation, the dogs were bred as usual, and in order to prevent dehydration, dietary salt (approx. 0.4 g/day) was mixed into feed, and given to the dogs.

Gastric Juice Secretion Measurement Method

The Heidenhain pouch dogs were used three weeks after the surgery. The dogs were deprived of feed for 18 hours or more in the situation in which water was given, and their gastric juice was collected with the dogs being hung with an abdominal bandage in a steel pipe frame. The gastric juice was collected every 15 minutes from 30 minutes before, to two hours after, secretory product administration, and the gastric juice volume (mL) and acidity (value measured by neutralizing titration technique with 0.01 N NaOH: mEq/L) were measured to calculate from the obtained gastric juice volume and acidity the secreted gastric juice amount (mEq/15 min) at each measuring time.

The results are set forth in Tables 1 through 4.

TABLE 1

Change of secreted gastric juice amount by administrating (test substance) A

| Experimental Group | Secretion amount (mg/kg) | n = 3 | secreted gastric juice amount (mEq/15 min) | | | | | | | | |
|---|---|---|---|---|---|---|---|---|---|---|---|
| | | | before administration | Inspection time after administration (min) | | | | | | | |
| | | | | 15 | 30 | 45 | 60 | 75 | 90 | 105 | 120 |
| Secretion (testsubstance)[A] | 10 | Average | 0.82 | 0.97 | 0.96 | 1.18 | 1.20* | 0.95 | 0.77 | 0.88* | 0.72 |
| | | standard deviation | 0.09 | 0.12 | 0.16 | 0.19 | 0.12 | 0.16 | 0.04 | 0.08 | 0.05 |

*P < 0.05; Significant difference with respect to before administration rate (Paired t-test)

TABLE 2

Change of secreted gastric juice amount by administrating secretion (test substance) A

| Experimental Group | Individual number | secreted gastric juice amount (mEq/15 min) | | | | | | | | |
|---|---|---|---|---|---|---|---|---|---|---|
| | | before administration | Inspection time after administration (min) | | | | | | | |
| | | | 15 | 30 | 45 | 60 | 75 | 90 | 105 | 120 |
| Secretion (testsubstance)[A] | 1 | 0.75 | 0.80 | 0.90 | 1.20 | 1.00 | 0.65 | 0.72 | 0.80 | 0.64 |
| | 2 | 1.00 | 1.20 | 1.25 | 1.50 | 1.40 | 1.20 | 0.84 | 1.05 | 0.80 |
| | 3 | 0.72 | 0.90 | 0.72 | 0.84 | 1.20 | 1.00 | 0.75 | 0.80 | 0.72 |

TABLE 3

Change of secreted gastric juice amount by administrating secretion (test substance) A

| | | | | secreted gastric juice amount (mEq/15 min) | | | | | | | |
|---|---|---|---|---|---|---|---|---|---|---|---|
| Experimental Group | Secretion amount | n = 3 | before administration | Inspection time after administration (min) | | | | | | | |
| | | | | 15 | 30 | 45 | 60 | 75 | 90 | 105 | 120 |
| meat extract | 25% | Average | 0.01 | 0.15 | 0.53 | 0.57 | 0.41 | 0.25 | 0.15 | 0.09 | 0.07 |
| | | standard deviation | 0.0 | 0.1 | 0.1 | 0.0 | 0.0 | 0.1 | 0.0 | 0.0 | 0.0 |

TABLE 4

Change of secreted gastric juice amount by administrating meat extract

| | | | secreted gastric juice amount (mEq/15 min) | | | | | | | |
|---|---|---|---|---|---|---|---|---|---|---|
| Experimental Group | Individual number | before administration | Inspection time after administration (min) | | | | | | | |
| | | | 15 | 30 | 45 | 60 | 75 | 90 | 105 | 120 |
| meat extract | 1 | 0.02 | 0.27 | 0.55 | 0.52 | 0.42 | 0.31 | 0.19 | 0.12 | 0.12 |
| | 2 | 0.02 | 0.16 | 0.61 | 0.57 | 0.32 | 0.31 | 0.20 | 0.11 | 0.07 |
| | 3 | 0.00 | 0.02 | 0.42 | 0.61 | 0.48 | 0.14 | 0.07 | 0.03 | 0.02 |

Results of administering the secretory product demonstrated gastric juice secretion amounts of 0.82 to 1.20 on an average before, and within two hours of, the secretory product administration, and demonstrated the largest increase in gastric acid secretion amount 60 minutes after the secretory product administration. The increment was 0.38 mEq/15 min.

Experimental results on individual dogs 1, 2, and 3 are set forth in Table 2. The results demonstrated statistically significant increases in gastric juice secretion amount 60 minutes and 105 minutes after the secretory product administration, compared with the gastric juice secretion amount before the administration. On an average, gastric juice secretion amounts were of 0.01 to 0.57 before, and within two hours of, meet extract administration (Tables 3 and 4). The amount of gastric acid secretion increased most largely 45 minutes after the meet extraction administration, and the increment was 0.56 mEq/15 min.

In the secretory product of the present invention, above examples showed statistically significant differences in gastric acid secretion 60 minutes and 105 minutes after the secretory product administration, and also showed a tendency for the gastric acid secretion to increase even 15, 30, 45 and 75 minutes after the gastric acid secretion administration, even though there was no statistically significant difference. Compared with the results of administering meet extract, the secretory product (test substance) administration results demonstrated slightly smaller increment than that in the meet extract administration results, but demonstrated at the time at which the gastric acid secretion most largely increased, the gastric acid secretion increase and decrease similar to those in the meet extract administration results. From these results, it is believed that the secretory product (test substance) is effective in increasing gastric juice secretion amount, and this effect was the same with that of the meat extract.

Third Embodiment

In embodiment 3 of the present invention, in order to search effectiveness of the secretory product to Xenograft model, study of influence of the secretory product on tumor cell line MKN-45 was attempted. The secretory product as test substance was administered subcutaneously in experimental animals for four weeks. As end points, weight measurement, tumor volume measurement, hematological test, and pathological test were carried out.

Experimental Overview

1. Experimental animal: Twenty animals 15.2 to 20.1 g in weigh—BALB/C-nu-type male mice purchased at the age of four weeks—were used. Through the experimental period, the animals were bred in an animal room arranged in a region in which a temperature was 20 to 26° C., a relative humidity was 40 to 70%, the times of ventilation was 10 to 20 times per hour, lighting hours were 12 hours.

2. Breeding conditions: Water and feed are freely taken.

3. Experimental groups: When tumors developed to have an average volume of 200 to 300 mm$^3$, the animals were divided into two groups.

4. Bulk powder of the product secreted by the novel microorganism was precisely weighed with a top-loading balance for highly precise analysis, and was dissolved into normal saline solution of 10 mL. All dosing solutions were prepared when used.

5. Tumor cell preparation: Cell culture solution was prepared by adding to medium penicillin-streptomycin of 100 u/mL to 100 μmL.

Cells that had been frozen were thawed in warm water of approx. 37° C. to transfer the cells to a centrifuge tube containing the culture solution previously incubated at temperature of 37° C. After the culture solution in which the cells were transferred was centrifuged at 1000 rpm for five minutes, supernatant was cleared out, and the culture solution was added to the cells, and suspended thoroughly by pipetting. Subsequently, the suspension was moved into a culture flask to start culture in a $CO_2$ incubator (MCO-175 from Sanyo Electric Co., Ltd) in which temperature was arranged to be 37° C., and carbon dioxide concentration was arranged to be 5%. In subcultivating the cells, the culture solution was removed from the incubator before cell density increased excessively, and the surfaces of the cells were cleaned with PBS solution. After that, the cells were added with 0.25% trypsin and 1 m MEDTA solution, put in the $CO_2$ incubator, and completely separated off. The separated cells were collected with a proper amount of culture solution, and the cells and culture solution were centrifuged at 1000 rpm for 5 minutes. Then, supernatant was removed, and culture solution was added to the cells, and pipetted. After that, the cells were seeded in a different culture flask containing the culture solution. Subcultivation was carried out as frequently as two to four days, the cells subcultitvated two times or more were used for transplantation.

6. Administration method: The test substances were subcutaneously administered dorsally in the mice once-daily for four weeks with a disposable syringe and a 27 G injection needle. The amount of dosing solution was calculated based on weights measured two times a week.

7. Tumor cells: Tumor cells were subcutaneously administered dorsally in the mice with the disposable syringe and 27 G injection needle on the day of transplantation.

In the foregoing experiment, normal condition of the mice and whether or not the mice were living were checked once a day, and their weights were measured twice a week. Furthermore, the tumor longest diameter (A) and shortest diameter (B) were measured twice a week with a digital caliper. From the measured longest and shortest diameters, tumor volume was calculated using the following expression.

$$\text{Tumor volume (mm}^3\text{)} = AB^2/2$$

Furthermore, hematological test was carried out. As to blood EDTA-2K-trated after taken from abdominal great veins of all the mice, the following inspection items were measured with an automatic hematology analyzer (Sysmex corporation, E-4000). The results are set forth in Table 5.

TABLE 5

| Inspection Item | Measuring Method or Instrument | Unit/Sign |
|---|---|---|
| Red blood cell (RBC) count | Electrical-resistance detection | $10^4/\mu L$ |
| Hematocrit (Ht) | Maximum erythroid pulse detection | % |
| Hemoglobin (Hb) content | SLS hemoglobin method | g/dL |
| Platelet (Plt) count | Electrical-resistance detection | $10^4/\mu L$ |
| White blood cell (WBC) count | Eectrical-resistance detection | $10^2/\mu L$ |
| Mean red blood cell index calculation method | | |
| Mean corpuscular volume (MCV) | $\dfrac{Ht(\%)}{RBC(10^4/\mu L)} \times 10^3$ | fL |
| Mean corpuscular hemoglobin (MCH) | $\dfrac{Hb(g/dL)}{RBC(10^4/\mu L)} \times 10^3$ | pg |

TABLE 5-continued

| Inspection Item | Measuring Method or Instrument | Unit/Sign |
|---|---|---|
| Mean corpuscular hemoglobin concentration (MCHC) | $\dfrac{Hb(g/dL)}{Ht(\%)} \times 10^2$ | % |

Pathology test: After the blood drawing was completed, tumor tissues were extirpated to measure their weights, and then were fixed with a neutral buffered formalin solution. After the fixing, paraffin sections were prepared in accordance with a normal method, and then were subjected to hematoxylin-eosin staining. Subsequently, by carrying out immunohistochemical staining (TUNEL), positive cells in 1000 tumor cells were counted to calculate the ratio positive cells/tumor cells.

Twenty mice were used to subcutaneously transplant tumors dorsally in the mice. After the tumor transplantation, when the tumor developed to have an average volume of approx. 200 to 300 mm, the mice were divided into two groups so that the average tumor volume in one group equals to that in another. The test substances were administered subcutaneously in the mice continuously for four weeks. From the day of the test substance administration, normal condition of the mice, and whether or not the mice were living were observed once-daily for four weeks, and weights of the mice and sizes of the tumors were measured twice a week. Four weeks after the test substance administration, blood of the mice was taken from their abdominal great veins under ether anesthesia, and tumor tissues were extirpated.

The foregoing test results will be described in detail.

1. Shifts in weight: Weight changes in the two groups for four weeks after the test substance administration were set forth in Tables 6 and 7. In both of the two groups: that of the groups in which normal saline solution was administered, and that of the groups in which the secretory product was administered, significant weight decreases were observed during the administration period. The peak of the weight decreases was on the twelfth day from the administration in the normal saline solution-administering group, and was on the second day from the administration in the secretory product-administering group. Compared with the weight on the first day from the administration, the normal saline solution-administering group experienced weight decrease of 1.9 g on the twelfth day, and the secretory product-administering group experienced weight decrease of 1.2 g on the second day.

TABLE 6

Influence of repeated oral dosing of secretory product (test substance) A for four weeks on weight in nude mouse antitumor test (MKN-45)

| Dosage material | sample number | | Weight (g) | | | | | | | | |
|---|---|---|---|---|---|---|---|---|---|---|---|
| | | | 1 | 5 | 8 | 12 | 15 | 19 | 22 | 26 | 29 (day) |
| Normal saline solution | 10 | Average | 18.1 | 17.2* | 17.3 | 16.2** | 16.3** | 16.5** | 16.3** | 16.7** | 17.4 |
| | | standard deviation | 0.4 | 0.4 | 0.4 | 0.4 | 0.5 | 0.4 | 0.4 | 0.5 | 0.5 |
| Secretion (testsubstance)[A] | 10 | Average | 19.3 | 19.2 | 19.1 | 18.6** | 18.2** | 18.2** | 18.1** | 18.6* | 19.4 |
| | | standard deviation | 0.5 | 0.6 | 0.6 | 0.5 | 0.5 | 0.4 | 0.5 | 0.5 | 0.5 |

*, **p < 0.05, 0.01 Significant difference with respect to before administration rate (Paired t test)

TABLE 7

Influence on four weeks repetition oral administration of the secretion which gives it to the weight in the antitumor examination of the nude mouse (MKN-45)

| Dosage material | Animal No. | Weight (g) | | | | | | | | |
|---|---|---|---|---|---|---|---|---|---|---|
| | | 1 | 5 | 8 | 12 | 15 | 19 | 22 | 26 | 29 (day) |
| Normal saline solution | 1 | 17.2 | 16.8 | 17.6 | 17.0 | 17.0 | 16.9 | 17.3 | 17.4 | 17.7 |
| | 2 | 17.8 | 16.3 | 16.0 | 14.9 | 14.9 | 15.1 | 14.5 | 15.0 | 15.9 |
| | 3 | 18.7 | 18.6 | 18.6 | 17.4 | 18.0 | 18.0 | 17.8 | 18.8 | 19.2 |
| | 4 | 18.0 | 16.4 | 16.6 | 15.6 | 15.6 | 15.7 | 15.6 | 16.4 | 17.7 |
| | 5 | 17.6 | 17.0 | 17.5 | 16.6 | 16.9 | 17.1 | 16.6 | 16.2 | 18.0 |
| | 6 | 17.7 | 16.4 | 16.2 | 15.1 | 15.1 | 15.7 | 15.8 | 16.2 | 16.8 |
| | 7 | 19.5 | 18.7 | 19.3 | 17.8 | 18.1 | 18.5 | 18.0 | 18.7 | 19.0 |
| | 8 | 16.9 | 18.3 | 17.9 | 16.0 | 15.9 | 16.8 | 16.5 | 16.8 | 17.2 |
| | 9 | 18.7 | 16.5 | 16.3 | 15.6 | 15.6 | 15.9 | 15.3 | 15.6 | 16.0 |
| | 10 | 18.5 | 17.4 | 17.2 | 15.9 | 15.8 | 15.7 | 15.7 | 16.0 | 16.5 |
| Secretion (testsubstance)[A] | 11 | 20.8 | 19.3 | 19.7 | 19.1 | 19.3 | 18.7 | 18.9 | 19.4 | 20.1 |
| | 12 | 17.7 | 17.6 | 17.3 | 16.7 | 16.5 | 16.8 | 16.3 | 17.3 | 17.9 |
| | 13 | 16.5 | 15.9 | 16.0 | 15.9 | 15.4 | 15.8 | 15.5 | 15.5 | 16.7 |
| | 14 | 21.3 | 20.9 | 20.7 | 20.2 | 19.5 | 19.1 | 18.7 | 18.5 | 18.8 |
| | 15 | 19.6 | 19.8 | 19.7 | 19.6 | 19.0 | 18.9 | 18.8 | 19.7 | 20.0 |
| | 16 | 19.6 | 19.6 | 19.1 | 18.7 | 18.0 | 18.4 | 17.8 | 18.4 | 19.4 |
| | 17 | 18.9 | 19.3 | 19.2 | 18.3 | 18.1 | 18.3 | 18.3 | 19.1 | 20.6 |
| | 18 | 18.5 | 18.5 | 18.7 | 18.0 | 17.5 | 17.5 | 17.7 | 18.2 | 19.2 |
| | 19 | 21.0 | 22.3 | 22.2 | 20.9 | 20.4 | 20.4 | 20.6 | 21.3 | 22.2 |
| | 20 | 19.1 | 18.4 | 18.5 | 18.3 | 18.2 | 18.3 | 18.2 | 18.1 | 19.3 |

2. Tumor weight measurement: Tumor volume changes within four weeks of the test substance administration are set forth in Tables 8 to 9. The normal saline solution-administering group demonstrated day-by-day tumor volume increase during the solution administration period. Also in the secretory product-administering group, the similar tumor volume increase to that in the normal saline solution-administering group was observed. Both of the two groups experienced no significant tumor volume increase on each measurement date.

TABLE 8

Influence of repeated oral dosing of secretory product (test substance) A for four weeks on tumor volume in nude mouse antitumor test (MKN-45)

| material | The number of the examples | | tumor volume (mm³) | | | | | | | | |
|---|---|---|---|---|---|---|---|---|---|---|---|
| | | | 1 | 5 | 8 | 12 | 15 | 19 | 22 | 26 | 29 (day) |
| Normal saline solution | 10 | Average | 255.9 | 382.5 | 478.5 | 584.3 | 729.5 | 920.1 | 1094.6 | 1255.9 | 1479.9 |
| | | standard deviation | 21.9 | 22.9 | 23.3 | 33.8 | 42.8 | 55.2 | 66.9 | 76.0 | 89.8 |
| Secretion (test substance)[A] | 10 | Average | 223.7 | 350.3 | 433.8 | 575.5 | 703.9 | 884.8 | 1014.1 | 1189.6 | 1412.2 |
| | | standard deviation | 21.8 | 33.8 | 37.2 | 49.4 | 69.3 | 87.0 | 92.8 | 125.3 | 142.8 |

TABLE 9

Influence of repeated oral dosing of secretory product (test substance) A for four weeks on hematological inspection in nude mouse antitumor test (MKN-45)

| Dosage material | Animal No. | tumor volume (mm³) | | | | | | | | |
|---|---|---|---|---|---|---|---|---|---|---|
| | | 1 | 5 | 8 | 12 | 15 | 19 | 22 | 26 | 29 (day) |
| Normal saline solution | 1 | 290.1 | 578.0 | 760.8 | 940.8 | 1136.2 | 1403.6 | 1811.6 | 1963.5 | 2216.8 |
| | 2 | 292.5 | 366.7 | 539.6 | 602.8 | 761.3 | 873.3 | 1207.1 | 1488.2 | 1851.3 |
| | 3 | 137.7 | 296.5 | 425.3 | 457.9 | 577.6 | 658.6 | 754.3 | 853.9 | 927.4 |
| | 4 | 193.9 | 309.0 | 348.0 | 524.3 | 629.3 | 719.3 | 901.6 | 1111.6 | 1432.1 |
| | 5 | 386.0 | 423.9 | 465.5 | 538.7 | 789.6 | 1074.6 | 1149.3 | 1362.9 | 1574.3 |
| | 6 | 252.4 | 342.4 | 433.4 | 593.0 | 621.9 | 780.4 | 899.2 | 951.7 | 1081.3 |
| | 7 | 234.5 | 371.2 | 465.7 | 543.3 | 685.6 | 875.5 | 1055.6 | 1204.0 | 1458.6 |
| | 8 | 215.1 | 282.4 | 377.4 | 408.9 | 533.3 | 792.4 | 957.2 | 1099.0 | 1325.4 |
| | 9 | 252.0 | 328.1 | 382.2 | 469.8 | 615.3 | 811.1 | 795.6 | 955.9 | 1207.3 |
| | 10 | 305.2 | 527.3 | 586.8 | 763.1 | 945.3 | 1212.3 | 1414.5 | 1568.1 | 1724.7 |
| (secretion test substance)[A] | 11 | 305.8 | 396.1 | 471.0 | 684.1 | 879.3 | 1050.8 | 1228.1 | 1326.9 | 1526.7 |
| | 12 | 321.4 | 445.5 | 536.2 | 686.7 | 804.8 | 958.2 | 1094.0 | 1617.4 | 1779.9 |
| | 13 | 256.0 | 379.5 | 405.0 | 450.6 | 540.7 | 821.5 | 915.1 | 990.9 | 1289.7 |
| | 14 | 169.0 | 306.6 | 366.1 | 539.3 | 652.9 | 767.3 | 843.7 | 941.5 | 1158.6 |

TABLE 9-continued

Influence of repeated oral dosing of secretory product (test substance) A
for four weeks on hematological inspection in nude mouse antitumor test (MKN-45)

| Dosage material | Animal No. | tumor volume (mm³) | | | | | | | | |
|---|---|---|---|---|---|---|---|---|---|---|
| | | 1 | 5 | 8 | 12 | 15 | 19 | 22 | 26 | 29 (day) |
| | 15 | 113.4 | 136.1 | 186.4 | 252.5 | 288.8 | 385.6 | 489.1 | 635.1 | 788.2 |
| | 16 | 245.0 | 436.4 | 564.1 | 766.4 | 993.7 | 1350.6 | 1453.8 | 1758.2 | 2002.8 |
| | 17 | 134.5 | 256.0 | 489.8 | 530.5 | 551.4 | 773.3 | 943.2 | 993.6 | 1146.9 |
| | 18 | 241.9 | 392.1 | 447.5 | 622.4 | 676.3 | 742.6 | 799.3 | 899.4 | 976.8 |
| | 19 | 210.8 | 326.1 | 402.7 | 605.0 | 819.3 | 984.6 | 1196.1 | 1495.0 | 1898.7 |
| | 20 | 239.1 | 428.5 | 469.3 | 617.2 | 831.7 | 1013.7 | 1178.6 | 1237.8 | 1553.7 |

3. Hematological test: Results of hematological test in the two groups within four weeks of the test substance administration are set forth in Tables 10 and 11. The secretory product-administering group experienced a more significant increase in platelet count among inspection items, compared with the saline solution administering-group, but neither normal saline solution-administering group nor the secretion-administering group experienced any significant increase in other seven inspection items.

TABLE 10

Influence of repeated oral dosing of secretory product (test substance) A for
four weeks on hematological inspection in nude mouse antitumor test (MKN-45)

| Administered substance | No. of Subjects | | RBC ($10^4/\mu L$) | Ht (%) | Hb (g/dL) | MCV (fL) | MCH (pg) | MCHC (%) | Plt ($10^4/\mu L$) | WBC ($10^2/\mu L$) |
|---|---|---|---|---|---|---|---|---|---|---|
| Normal saline solution | 10 | Average | 1046.6 | 46.7 | 15.5 | 44.7 | 14.8 | 33.1 | 76.0 | 16.8 |
| | | ± standard deviation | 9.3 | 0.4 | 0.2 | 0.3 | 0.2 | 0.3 | 2.7 | 1.8 |
| Secretion(test substance)[4] | 10 | Average | 1040.6 | 45.6 | 14.9 | 43.9 | 14.3 | 32.7 | 94.0## | 23.3 |
| | | ± standard deviation | 12.5 | 0.5 | 0.2 | 0.3 | 0.2 | 0.4 | 2.8 | 3.8 |

RBC: red blood cell count,
Ht: hematocrit,
Hb: hemoglobin content,
MCV: mean corpuscular volume,
MCH: mean corpuscular hemoglobin,
MCHC: mean corpuscular hemoglobin concentration,
Plt: platelet count,
WBC: white blood cell count
, ##p < 0.05, 0.01 significant difference with respect to normal saline solution (student t test)

TABLE 11

Influence of repeated oral dosing of secretory product
(test substance) A for four weeks on hematological
inspection in nude mouse antitumor test (MKN-45)

| Dosage material | Animal No. | RBC ($10^4/\mu L$) | Ht (%) | Hb (g/dL) | MCV (fL) | MCH (pg) | MCHC (%) | Plt ($10^4/\mu L$) | WBC ($10^2/\mu L$) |
|---|---|---|---|---|---|---|---|---|---|
| Normal saline solution | 1 | 1030 | 46.7 | 15.3 | 45.3 | 14.9 | 32.8 | 88.0 | 23 |
| | 2 | 1051 | 46.1 | 15.6 | 43.9 | 14.8 | 33.8 | 59.5 | 19 |
| | 3 | 1012 | 46.0 | 14.9 | 45.5 | 14.7 | 32.4 | 73.0 | 12 |
| | 4 | 1019 | 44.5 | 14.6 | 43.7 | 14.3 | 32.8 | 77.8 | 10 |
| | 5 | 1078 | 47.6 | 15.6 | 44.2 | 14.5 | 32.8 | 82.1 | 21 |
| | 6 | 1030 | 45.4 | 14.7 | 44.1 | 14.3 | 32.4 | 71.3 | 10 |
| | 7 | 1101 | 48.4 | 15.7 | 44.0 | 14.3 | 32.4 | 82.4 | 11 |
| | 8 | 1044 | 48.4 | 17.0 | 46.4 | 16.3 | 35.1 | 69.4 | 15 |
| | 9 | 1026 | 45.8 | 15.7 | 44.6 | 15.3 | 34.3 | 72.1 | 23 |
| | 10 | 1075 | 48.3 | 15.5 | 44.9 | 14.4 | 32.1 | 84.0 | 24 |
| Secretion (test substance)[4] | 11 | 1061 | 46.0 | 14.0 | 43.4 | 13.2 | 30.4 | 90.7 | 19 |
| | 12 | 991 | 44.6 | 14.9 | 45.0 | 15.0 | 33.4 | 89.5 | 53 |
| | 13 | 1021 | 46.5 | 14.9 | 45.5 | 14.6 | 32.0 | 94.1 | 23 |
| | 14 | 1118 | 48.0 | 15.6 | 42.9 | 14.0 | 32.5 | 90.6 | 15 |
| | 15 | 998 | 44.7 | 14.3 | 44.8 | 14.3 | 32.0 | 104.6 | 28 |
| | 16 | 1053 | 45.3 | 15.1 | 43.0 | 14.3 | 33.3 | 100.0 | 22 |
| | 17 | 1001 | 43.3 | 14.3 | 43.3 | 14.3 | 33.0 | 109.1 | 10 |
| | 18 | 1074 | 47.7 | 15.5 | 44.4 | 14.4 | 32.5 | 94.1 | 28 |

TABLE 11-continued

Influence of repeated oral dosing of secretory product
(test substance) A for four weeks on hematological
inspection in nude mouse antitumor test (MKN-45)

| Dosage material | Animal No. | RBC ($10^4/\mu L$) | Ht (%) | Hb (g/dL) | MCV (fL) | MCH (pg) | MCHC (%) | Plt ($10^4/\mu L$) | WBC ($10^2/\mu L$) |
|---|---|---|---|---|---|---|---|---|---|
| | 19 | 1049 | 45.1 | 15.9 | 43.0 | 15.2 | 35.3 | 89.6 | 12 |
| | 20 | 1040 | 45.1 | 14.7 | 43.4 | 14.1 | 32.6 | 77.9 | 23 |

RBC: red blood cell count,
Ht: hematocrit,
Hb: hemoglobin,
MCV: mean corpuscular volume,
MCH: mean corpuscular hemoglobin,
MCHC: mean corpuscular hemoglobin concentration,
Plt: platelet count,
WBC: white blood cell count 4. Tumor weight measurement: Changes of tumor weight measured 4 weeks after the test substance administration are set forth in Tables 12 and 13. The tumor weights in the normal saline solution-administering and secretion-administering groups were respectively 0.093±0.109 g and 1.022±0.016 g, and neither of the two groups experienced significant tumor weight changes.

TABLE 12

Influence of repeated oral dosing of secretory product
(test substance)A for four weeks on tumor weight in
nude mouse antitumor test (MKN-45)

| Dosage material | sample No. | | tumor weight (g) |
|---|---|---|---|
| Normal saline solution | 10 | Average ± standard deviation | 1.093 ± 0.109 |
| Secretion (test substance)A | 10 | Average ± standard deviation | 1.022 ± 0.016 |

TABLE 13

Influence of repeated oral dosing of secretory product
(test substance)A for four weeks on tumor weight in
nude mouse antitumor test(MKN-45)

| Dosage material | Animal No. | tumor weight (g) |
|---|---|---|
| Normal saline solution | 1 | 1.665 |
| | 2 | 1.534 |

TABLE 13-continued

Influence of repeated oral dosing of secretory product
(test substance)A for four weeks on tumor weight in
nude mouse antitumor test(MKN-45)

| Dosage material | Animal No. | tumor weight (g) |
|---|---|---|
| | 3 | 0.925 |
| | 4 | 1.006 |
| | 5 | 0.605 |
| | 6 | 0.599 |
| | 7 | 1.141 |
| | 8 | 1.099 |
| | 9 | 1.220 |
| | 10 | 1.140 |
| Secretion (test substance)$^A$ | 11 | 1.174 |
| | 12 | 0.905 |
| | 13 | 0.937 |
| | 14 | 1.026 |
| | 15 | 0.751 |
| | 16 | 1.613 |
| | 17 | 1.047 |
| | 18 | 0.595 |
| | 19 | 1.658 |
| | 20 | 0.511 |

5. Pathological test: Average values in the two groups in pathological test within four weeks of the test substance administration are set forth in Tables 14 and 15. Results of calculating the ratio positive cells/tumor cells in the normal saline solution-administering and secretion-administering groups demonstrated no numerical significant change.

TABLE 14

Influence of repeated oral dosing of secretory product (test substance)A
for four weeks on illness physical examination in nude mouse antitumor test (MKN-45)

| | | | Dosage material | |
|---|---|---|---|---|
| parameter | | number of sample | Normal saline solution 10 | Secretion (test substance)$^A$ 10 |
| Histological grade | | Grade | | |
| No therapeutic effects observed | | 0 | 10 (100.0)$^c$ | 10 (100) |
| Degenerative changes in tumor cells, but no destruction of tumor nests | | I | 0 | 0 |
| Destruction and disappearance of tumor nests, but viable cells remain | | | | |
| viable cells occupy large areas (≥⅓) | | IIa | 0 | 0 |
| viable cells occupy small areas (<⅓) | | IIb | 0 | 0 |

TABLE 14-continued

Influence of repeated oral dosing of secretory product (test substance)A
for four weeks on illness physical examination in nude mouse antitumor test (MKN-45)

| | | Dosage material | |
|---|---|---|---|
| parameter | number of sample | Normal saline solution 10 | Secretion (test substance)[d] 10 |
| Tumor cells remain but appear non-viable | III | 0 | 0 |
| No tumor cells remain | IV | 0 | 0 |
| TUNEL[d] index (% Average ± standard deviation) | | 1.17 ± 0.16 | 1.09 ± 0.08 |

[c]Value in parenthesis indicates the % incidence
[d]TdT (terminal deoxynucleotidyl transferase) mediated dUTP-biotin Nick End Labeling

TABLE 15

Influence of repeated oral dosing of secretory product (test substance) A
for four weeks on illness physical examination in nude mouse antitumor test (MKN-45)

| Dosage material | Animal No. | Organs/tissues | Findings | Histological grade | TUNEL index (%) |
|---|---|---|---|---|---|
| Normal saline solution | 1 | Tumor | No therapeutic effects observed | 0 | 1.6 |
| | 2 | Tumor | No therapeutic effects observed | | 1.2 |
| | 3 | Tumor | No therapeutic effects observed | 0 | 0.7 |
| | 4 | Tumor | No therapeutic effects observed | 0 | 1.2 |
| | 5 | Tumor | No therapeutic effects observed | 0 | 2.4 |
| | 6 | Tumor | No therapeutic effects observed | 0 | 0.9 |
| | 7 | Tumor | No therapeutic effects observed | 0 | 1.3 |
| | 8 | Tumor | No therapeutic effects observed | 0 | 0.8 |
| | 9 | Tumor | No therapeutic effects observed | 0 | 0.9 |
| | 10 | Tumor | No therapeutic effects observed | 0 | 0.7 |
| | Average | | | | 1.17 |
| | standard deviation | | | | 0.16 |
| Secretion (test substance)[d] | 11 | Tumor | No therapeutic effects observed | 0 | 0.9 |
| | 12 | Tumor | No therapeutic effects observed | 0 | 1.3 |
| | 13 | Tumor | No therapeutic effects observed | 0 | 1.0 |
| | 14 | Tumor | No therapeutic effects observed | 0 | 0.8 |
| | 15 | Tumor | No therapeutic effects observed | 0 | 0.9 |
| | 16 | Tumor | No therapeutic effects observed | 0 | 1.5 |
| | 17 | Tumor | No therapeutic effects observed | 0 | 1.2 |
| | 18 | Tumor | No therapeutic effects observed | 0 | 1.3 |
| | 19 | Tumor | No therapeutic effects observed | 0 | 1.2 |
| | 20 | Tumor | No therapeutic effects observed | 0 | 0.8 |
| | Average | | | | 1.09 |
| | standard deviation | | | | 0.08 |

In both of the normal saline solution-administering and secretory product-administering groups, as to weight during the administration period, above results demonstrated weight decrease until the second or third day from the administration, but showed a tendency of regaining the weight on the first day of the administration after the second or third day from the administration. Such a weight decrease is believed to occur under the influence of the tumor transplantation, not of the test substance, because the normal saline solution-administering group also experiences the weight decrease. As to tumor volume, in the normal saline solution-administering and secretory product-administering groups, a tumor volume increase similar to the tumor weight increase was observed during the administration period, and a tumor volume decrease caused by secretory product administration was not demonstrated. In the hematological test, the secretory product-administering group experienced a significant increase in platelet count. These results made it clear that the secretory product of the present invention dose not have activity increasing tumor cells. Accordingly, it is apparent that the secretory product of the present invention can be safely given even to patients with stomach cancer and other tumors in digestive system in order to increase gastric juice of the patients.

In addition, although the weight decrease was demonstrated until the second or third day from the administration, no significant change was experienced. Tumor weight measurement: Tumor weight changes in the two groups within four weeks of the test substance administration are set forth in Tables 8 and 9. The normal saline solution-administering group demonstrated a day-by-day tumor volume increase during the administration period. Also in the secretory product-administrating group, a similar tumor volume increase to that in the normal saline solution-administering group was observed. Neither of the two groups experienced any significant tumor volume increase.

Fourth Embodiment

Figure 10:
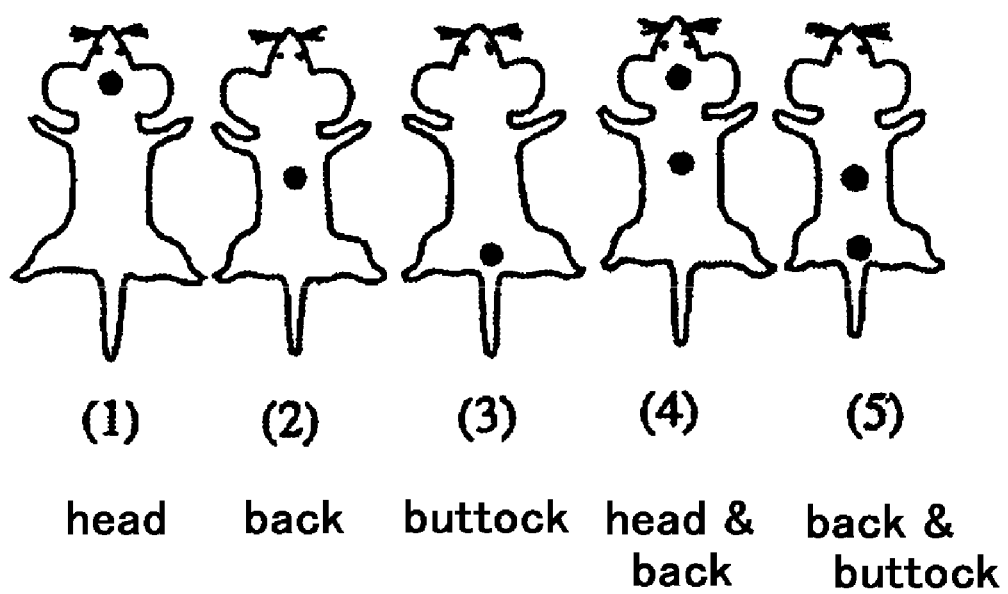
FIG. 10 is a diagram representing an individual identifying method in which pigment is applied to mouse fur.

Embodiment 4 (single subcutaneous dose toxicity test on mice with the product secreted by the novel microorganism) of the present invention will be described with FIG. 10. In this test, a study was made as to lethal dose and toxicological appearance in the situation in which the product secreted by the novel microorganism was subcutaneously administered in the mice one time.

Secretory Product from Present-Invention Novel Microorganism Employed

1. Characteristics: brownish-yellow colored; acicular crystalline.
2. Solubility: Soluble in distilled water, and in 5% dextrose in water.
3. Stability: Stable because not hydrolyzable, air-oxidizing, photodegradable, or thermally degradable. At a pH of 8 or more, however, becomes clouded.
4. Storing conditions: Hermetically sealed (with a desiccant being included) at room temperature.
5. Storing location: Stored in a room-temperature cabinet.

Experimental Mice

1. Species, genealogy, sex: mouse {Slc:ICR}, SPF animal, male
   2. Age in week: Mice that are four weeks old are grouped at the age of 5 weeks to start using the mice at the age of 6 weeks.
   3. Weights of the mice when they are grouped: 29.4 to 33.9 g
   4. Breeding environment conditions: A temperature is from 22.2 to 22.7° C.; a relative humidity is from 48.6 to 64.2%; RH•light-dark cycle is 12 hours; the times of ventilation is 10 times per hour; and feed and drinking water are taken freely.
   5. Individual identification: In 5 animals in each of the administrating groups, fur of the mice illustrated in FIG. 10 was applied with pigment by employing saturated picric acid solution to perform individual identification.
   6. Dosing solution adjusting method: After the secretory product and solvent (distilled water) were weighed, they were gradually blended, crushed and made cloud, and then were rendered a predetermined amount of dosing solution.
   7. Dosing solution amount: the dosing solution weight and grouping as shown in Table 5 with 2000 mg/kg that was the upper limit in guideline for non-clinical trials for pharmaceuticals being defined as high dose, dosing solution weight was 1,000 mg/kg half of the high dose, and a control (comparative group) was arranged.
   8. Administration Method: Dosing solution was subcutaneously administered, and in both the administering groups, dosing solution of 20 mL/kg was administered. Each dosing solution calculated from weight right before the administration was administered subcutaneously in backs of necks of the mice with a syringe on which a 26 G needle was put. Administration period was determined to be only one time on the first day (Day 1), and the administration was carried out in the morning.
   9. Observation period: Observation period was determined to be until the fifteenth day with the day of administration as the first day. As to when observation was carried out, whether or not the mice were living and normal condition of the mice were observed right after the administration, 1, 2, 4, and 6 hours after the administration only on the first day. On days other than the day of administration, whether or not the mice were living and normal condition of the mice were observed in the morning, and in the afternoon, only whether or not the mice were living was checked. In observing the normal condition, whether or not the mice was abnormal in appearance (fur, eyes, ears, nose, anus, and vulvar), behavior, posture, breathing, muscle stress, and enteruria, and the extent of the abnormality were observed with the naked eye, and weights of the mice were measured.
   10. Pathology inspection: There is no fatal case in the test. The survived mice in the groups therefore were abdominally operated on the fifteenth day under pentobarbital sodium salt anesthesia (100 mg/kg, intraperitoneal administration), and the abdominal great arterio-veins of the mice were cut to euthanize the mice by exsanguinations. After that, the mice were quickly dissected in accordance with pathological manner to observe organs and tissues on the surfaces of the bodies and in orifices, brainpans, chest cavities and abdominal cavities.

As a result of the experiment, the following became evident.

1. Incidence of Animal Death

Neither of the groups experienced death nor moribund condition of the mice.

2. Normal Condition

Neither of the groups experienced changes in normal condition of the mice.

3. Shifts in Weight

The group in which dosing solution of 1,000 mg/kg was administered and the group in which dosing solution of 2,000 mg/kg was administered showed a (slight) decrease in weight on the day after the administration. In the 2,000 mg/kg administering group experienced a significant decrease, compared with the comparative group. Herein, weight changes in the 1,000 mg/kg and 2,000 mg/kg administering groups from the third day to the fifteenth day were increase similar to those in the comparative group.

4. Pathology Inspection

In 2/5 cases in the 1,000 mg/kg administering group and 5/5 cases in the 2,000 mg/kg administering group, green-brown (slight) deposition that seemed to be secretory product was found in a site of the administration (subcutaneous tissue of the back of neck) depending on dosing solution weight. Furthermore, 1/5 cases in the 1000 mg/kg administering group experienced (left) testis (slight) diminishing. Abnormal findings other than the testis diminishing were not observed.

From the foregoing results, in the study of the lethal dose and toxicological appearance in the situation in which secretory product was administered one time subcutaneously in the mice to observe the mice for 15 days, although the weights of the mice on the second day (slightly) decreased depending on the dosing solution weight, weight changes similar to those in the comparative group was observed after the third day, so that is was believed that administering secretory product had a slight degree of influence on the weight changes. In the pathological inspection, although the fact that a (slight) deposition that seemed to be remaining secretory product was found on the site of administration suggested that the secretory product was not be subcutaneously absorbed well, the secretory product was presumably weak irritant because in the site of administration, changes such as inflammatory reaction was not observed. Furthermore, there were not any abnormal findings in other observation sites in the pathological inspection, so that clear toxicity changes originating in the exertion were not found.

From above results, it was apparent that the minimum lethal dose was 2,000 mg/kg or more because there were not any clear toxicity changes originating in the secretory products, and furthermore, moribund or dead animals were not found. Accordingly, the microorganism secretory product of the present invention is nontoxic, and thus can be used for treatment.

Fifth Embodiment

Embodiment 5 of the present invention will be explained.

Case 1

In case 1, Results of subcutaneously injecting a patient A under treatment for *Helicobacter pylori* with the novel microorganism of the present invention, together with *Helicobacter pylori* bacteria scavenging agent.

Preparation method: The secretory product was extracted in the same manner as in Embodiment 2.

Administration Method: The secretory product of 0.2 g and a normal saline solution were mixed, and administered by subcutaneously injecting the patient A with the mixture twice a day for seven days.

Results: The patient A showed gastric improvement 8 days later. The novel microorganism was viewed in any section collected from gastric wall under a microscope. The stomach felt light and free from something lying, heartburn did not occur next morning. Stomach condition was sufficiently improved.

Sixth Embodiment

Embodiment 6 of the present invention will be explained. When the section collected in Embodiment 5 was subjected to Giemsa staining, the novel microorganism of the present invention was confirmed to make figure-eight movement under a microscope.

INDUSTRIAL APPLICABILITY

According to the present invention, the novel microorganism was confirmed from the experiments to be able to promote gastric juice secretion, and furthermore, to be nontoxic. The present invention therefore has industrial applicability.

The material in the text file entitled "UY004_SeqList," created on Aug. 2, 2010, 3 kilobytes in size, and electronically submitted as part of the application of which this specification forms an essential part, is hereby incorporated by reference.

What is claimed is:

1. A biologically pure culture of the strain *Bacillus pumilus* NITE BP-295, isolated from either the human stomach wall or from human blood wherein said strain is gastric-juice promoting and nontoxic.

2. The *Bacillus pumilus* NITE BP-295 set forth in claim 1, characterized in taking the form of cocci as well as rods.

3. The *Bacillus pumilus* NITE BP-295 set forth in claim 1, further characterized in having the following bacteriological properties:

(1) being Gram-positive;
(2) being non-photodegradable;
(3) being motile;
(4) having a flagellum on each end;
(5) being aerobic;
(6) being 0.5 to 1 µm×10 to 20 µm in size; and
(7) being non-pyrogenic.

* * * * *

SEQUENCE LISTING

```
<160> NUMBER OF SEQ ID NOS: 1

<210> SEQ ID NO 1
<211> LENGTH: 1480
<212> TYPE: DNA
<213> ORGANISM: Bacillus pumilus

<400> SEQUENCE: 1
tcgagcggac agaagggagc ttgctcccgg atgttagcgg cggacgggtg agtaacacgt      60
gggtaacctg cctgtaagac tgggataact ccgggaaacc ggagctaata ccggatagtt     120
ccttgaaccg catggttcaa ggatgaaaga cggtttcggc tgtcacttac agatggaccc     180
gcggcgcatt agctagttgg tggggtaatg gctcaccaag gcgacgatgc gtagccgacc     240
tgagagggtg atcggccaca ctgggactga gacacggccc agactcctac gggaggcagc     300
agtagggaat cttccgcaat ggacgaaagt ctgacggagc aacgccgcgt gagtgatgaa     360
ggttttcgga tcgtaaagct ctgttgttag ggaagaacaa gtgcgagagt aactgctcgc     420
accttgacgg tacctaacca gaaagccacg gctaactacg tgccagcagc cgcggtaata     480
cgtaggtggc aagcgttgtc cggaattatt gggcgtaaag ggctcgcagg cggtttctta     540
agtctgatgt gaaagccccc ggctcaaccg gggagggtca ttggaaactg ggaaacttga     600
gtgcagaaga ggagagtgga attccacgtg tagcggtgaa atgcgtagag atgtggagga     660
acaccagtgg cgaaggcgac tctctggtct gtaactgacg ctgaggagcg aaagcgtggg     720
gagcgaacag gattagatac cctggtagtc cacgccgtaa acgatgagtg ctaagtgtta     780
gggggtttcc gcccttagt gctgcagcta acgcattaag cactccgcct ggggagtacg     840
gtcgcaagac tgaaactcaa aggaattgac ggggcccgc acaagcggtg gagcatgtgg     900
tttaattcga agcaacgcga agaaccttac caggtcttga catcctctga caaccctaga     960
gatagggctt tcccttcggg gacagagtga caggtggtgc atggttgtcg tcagctcgtg    1020
tcgtgagatg ttgggttaag tcccgcaacg agcgcaaccc ttgatcttag ttgccagcat    1080
tcagttgggc actctaaggt gactgccggt gacaaaccgg aggaaggtgg ggatgacgtc    1140
aaatcatcat gccccttatg acctgggcta cacacgtgct acaatggaca gaacaaaggg    1200
ctgcaagacc gcaaggttta gccaatccca taaatctgtt ctcagttcgg atcgcagtct    1260
```

-continued

```
gcaactcgac tgcgtgaagc tggaatcgct agtaatcgcg gatcagcatg ccgcggtgaa    1320
tacgttcccg ggccttgtac acaccgcccg tcacaccacg agagtttgca acacccgaag    1380
tcggtgaggt aacctttatg gagccagccg ccgaaggtgg ggcagatgat tggggtgaag    1440
tcgtaacaag gtagccgtat cggaaggtgc ggctggatca                          1480
```